US00PP26126P2

(12) United States Plant Patent
de Vos

(10) Patent No.: US PP26,126 P2
(45) Date of Patent: Nov. 24, 2015

(54) ***ABELIA* PLANT NAMED 'WEVO1'**

(50) Latin Name: *Abelia×grandiflora*
Varietal Denomination: Wevo1

(71) Applicant: Landert de Vos, Reeuwijk (NL)

(72) Inventor: Landert de Vos, Reeuwijk (NL)

( * ) Notice: Subject to any disclaimer, the term of this patent is extended or adjusted under 35 U.S.C. 154(b) by 187 days.

(21) Appl. No.: 13/987,614

(22) Filed: Aug. 14, 2013

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

(56) References Cited

PUBLICATIONS

UPOV Record Detail 'Wevo1', retrieved from UPOV website Jan. 20, 2015.*

* cited by examiner

*Primary Examiner* — Keith O. Robinson
(74) *Attorney, Agent, or Firm* — Penny J. Aguirre

(57) ABSTRACT

A new cultivar of *Abelia×grandiflora* named 'Wevo1' that is characterized by its mature foliage that is variegated with green centers and white margins; the variegation is retained from spring until winter, its white flowers, and its dwarf and upright spreading plant habit.

2 Drawing Sheets

Botanical classification: *Abelia×grandiflora.*
Varietal denomination: 'Wevo1'.

BACKGROUND OF THE INVENTION

The present invention relates to a new and distinct cultivar of *Abelia×grandiflora* and will be referred to hereafter by its cultivar name, 'Wevo1'. 'Wevo1' represents a new *Abelia*, a semi-evergreen shrub grown for landscape use.

The Inventor discovered the new cultivar in June of 2008 as a naturally occurring branch mutation of *Abelia×grandiflora* 'Abelops' (U.S. Plant Pat. No. 20,961) that was growing in a container at his nursery in Reeuwijk, The Netherlands.

Asexual propagation of the new cultivar was first accomplished by stem cuttings by the Inventor in Reeuwijk, The Netherlands in July of 2008. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Wevo1' as a unique cultivar of *Abelia.*

1. 'Wevo1' exhibits mature foliage that is variegated with green centers and white margins; the variegation is retained from spring until winter.
2. 'Wevo1' exhibits white flowers.
3. 'Wevo1' exhibits a dwarf and upright spreading plant habit; reaching about 1 m in height when mature.

'Abelops', the parent plant of 'Wevo1', differs from 'Wevo1' in having variegated foliage in which the white margin is wider, in having foliage that turns reddish in autumn, and in having flowers that are pinkish white in color. 'Wevo1' can also be compared to the cultivars 'Kaleidoscope' (U.S. Plant Pat. No. 16,988), 'Wevo2' (U.S. Plant Pat. No. 24,838) and 'Raspberry Profusion' (U.S. Plant Pat. No. 18,834). 'Wevo2' differs from 'Wevo1' in having foliage with a much thinner white margin. 'Kaleidoscope' differs from 'Wevo1' in having variegated foliage with green centers and wide yellow margins early in season with the leaves flushed with orange and red in autumn. 'Raspberry Profusion' differs from 'Wevo1' in having foliage that is non variegated and in having pink flowers.

BRIEF DESCRIPTION OF THE PHOTOGRAPHS

The plants and plant parts in the photographs depict a two-year old plant of 'Wevo1' as grown in an unheated greenhouse in a 15-cm container in Reeuwijk, The Netherlands.

Figure 1:
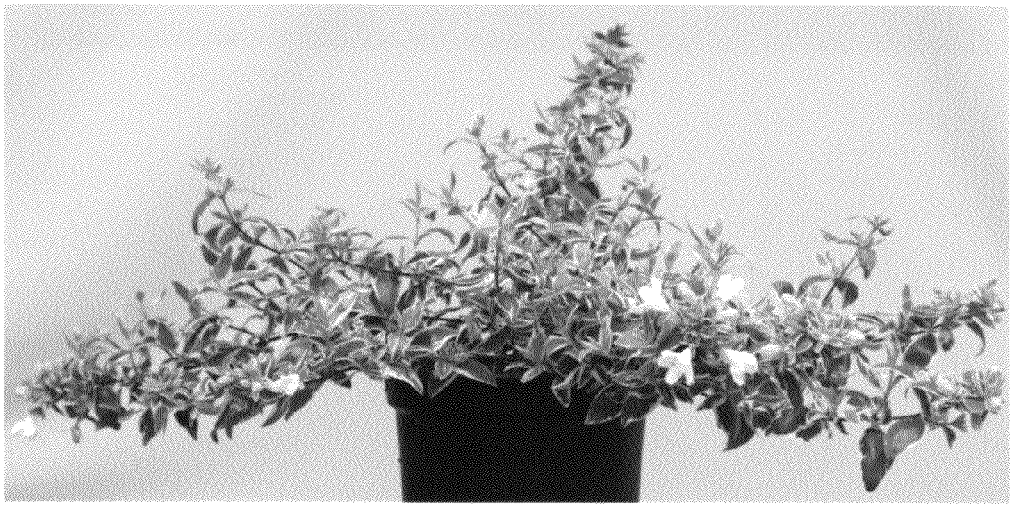

The photograph in FIG. 1 provides a side view of 'Wevo1'.

Figure 2:
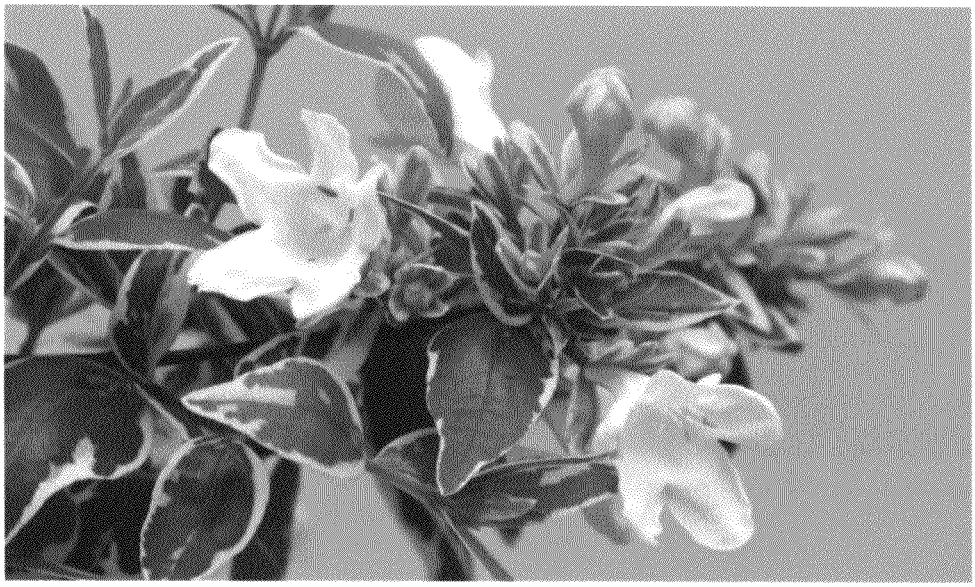

The photograph in FIG. 2 provides a close-up view of the flowers of 'Wevo1'.

Figure 3:
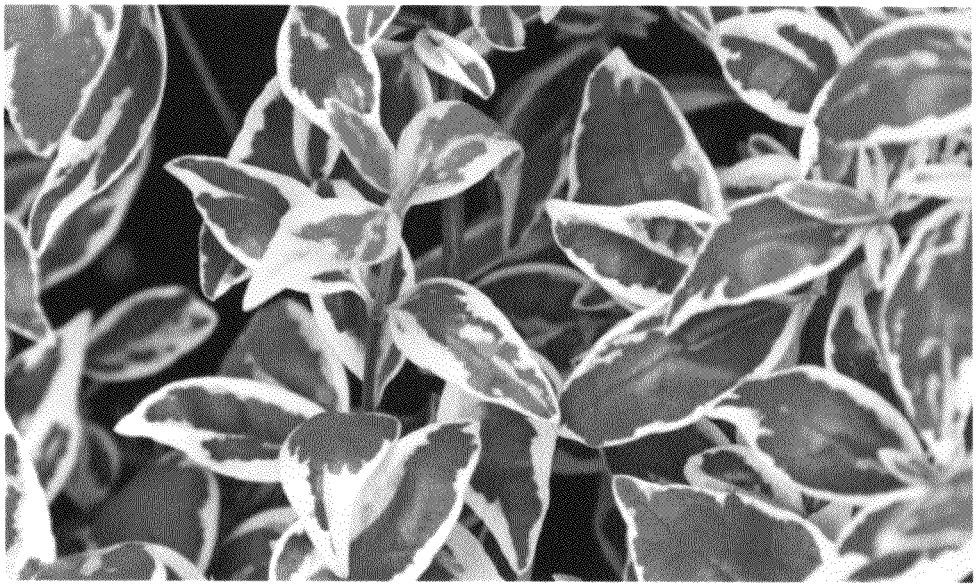

The photograph in FIG. 3 provides a close-up of the foliage of 'Wevo1'.

The colors in the photographs are as close as possible with the photographic and printing technology utilized and the color values cited in the detailed botanical description accurately describe the colors of the new *Abelia.*

DETAILED BOTANICAL DESCRIPTION

The following is a detailed description of two year-old plants of the new cultivar as grown in an unheated greenhouse in 15-cm containers in Reeuwijk, The Netherlands with average day temperatures ranging from 10° C. to 24° C. and average night temperatures ranging from 2° C. to 14° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late summer to autumn in The Netherlands.

*Plant type.*—Semi-evergreen shrub.

*Plant habit.*—Dwarf, spreading and broadly upright.

*Height and spread.*—Average of 20.4 cm in height and 47.4 cm in spread in as grown in a 15-cm container, reaching about 1 m in height and width in the landscape.

*Cold hardiness.*—At least to USDA Zone 7a.

*Diseases and pests.*—No susceptibility or resistance to pests and diseases has been observed.

*Root description.*—Fine, fibrous, and 158A in color.

*Propagation.*—Stem cuttings.

*Time required for root development.*—Roots initiate in about 30 days at 20° C. and fully develop in a about 2 months as a young rooted plant at 20° C.

*Growth rate.*—Moderate.

Stem description (main branches and lateral branches):

*Stem color.*—Young and mature stems; 183A.

*Stem size.*—Main stems; an average of 17.4 cm in length and 2 mm in diameter, lateral branches; an average of 7 cm in length and 2 mm in diameter.

*Stem quantity.*—Average of 20 basal branches and 4 to 5 lateral branches per main branch.

*Stem shape.*—Rounded.

*Stem surface.*—Moderately glossy with densely pubescent very short glandular hairs, average of 0.1 mm in length and to short to be measured with RHS-CC.

*Stem aspect.*—Very strong, held horizontal to upward with lateral stems held at about a 45° angle to main stems.

*Internode.*—Average of 2.4 cm in length.

*Branching habit.*—Free branching.

Foliage description:

*Leaf division.*—Single.

*Leaf attachment.*—Petiolate.

*Leaf arrangement.*—Opposite.

*Leaf number.*—Average of 14 (7 pairs).

*Leaf shape.*—Ovate.

*Leaf apex.*—Acute.

*Leaf surface.*—Both surfaces smooth and glossy.

*Leaf base.*—Rounded to short attenuate.

*Leaf venation.*—Pinnate, color upper surface; between N137C and 147A, color lower surface; 138B.

*Leaf margin.*—Entire to un-deeply and irregularly sinuate.

*Leaf color.*—Immature upper surface; 137C with irregular margins and occasional blotches 1C to 1D and 154C to 154D, immature lower surface; 138B with irregular margins and occasional blotches 154C to 154D, mature upper surface; N137C and 147A with irregular margins and occasional blotches ranging between 155A and 157D, mature lower surface; ranging between 147B and 191A with irregular margins and occasional blotches 155A, 157C and 157D.

*Leaf size.*—Average of 3.5 cm in length and 1.7 cm in width.

*Petioles.*—Average of 1 mm in diameter and 2.5 mm in length, both surfaces 147B to 147C in color, moderately glossy and densely pubescent with very short glandular hairs; an average of 0.1 mm in length.

Flower description:

*Inflorescence type.*—Numerous single flowers arranged on terminal panicles.

*Inflorescence aspect.*—All directions.

*Inflorescence size.*—Average of 4.9 cm in height and 5.9 cm in width.

*Flower fragrance.*—Faint, sweet.

*Flower quantity.*—Average of 16 per inflorescence.

*Flower lastingness.*—Average of 5 days.

*Flower buds.*—Obovate in shape, slightly curved downward, average of 6 mm in diameter and 1.5 cm in length, color; N155C, top 150C to 150D, base 145D, moderately glossy surface covered with very short glandular hairs, an average of 0.1 mm in length.

*Flower aspect.*—All directions.

*Flower shape.*—Irregular campanulate.

*Flower size.*—About 2.5 cm in depth and 2.2 cm in diameter.

*Petals.*—Average of 5, oblong in shape, margin is entire, apex is obtuse, upper surface is smooth and covered with soft hairs and are 1 mm in length and NN155C to NN155D in color, lower surface smooth and slightly glossy, color: upper surface when opening; 155A to 155B, center flushed with 76C, base 145D, lower surface when opening; 155B to 155C, center flushed with 76D, base 145D, upper surface when fully opened; NN155B to NN155C, center very slightly flushed with 76D, base 145D, lower surface when fully opened; NN155B, center very slightly flushed with 76D, base 145D, average of 2.1 cm in length and 7 mm in width, 55% of the lower petals fused.

*Calyx.*—Persistent, ornamental, rotate, average of 6 mm in length and 1.3 cm in diameter.

*Sepals.*—5, occasionally 2 or 3 sepals are fused, narrow elliptic in shape, margin is entire, apex is obtuse, base is cuneate, upper and lower surfaces are smooth and dull, color: immature upper surface; 147C, irregular margins a blend of 150D and 154D in color, immature lower surface; a blend of 146C and 147C, irregular margins a blend of 150D and 154D, mature upper and lower surfaces; 147C, irregular margins 155A, flushed with 63D, about 3 mm in width and 9 mm in length.

*Peduncles.*—Average of 3.4 cm in length and 1.25 mm in width, strong, color: upper surface; 183B to 183C, lower surface; 176B, glabrous surface, average angle of 0° (straight on top of lateral branch), secondary peduncles in an average angle of 45°.

*Pedicels.*—About 1 mm in length and 0.5 mm in width, strong, upper and lower surface 137C in color, glabrous surface, average angle: 0° (straight on top of peduncle), secondary pedicels in an average angle of 45°.

Reproductive organs:

*Gynoecium.*—1 pistil, club-shaped, about 1.8 mm in length, stigma, three-cleft, NN155C to NN155D in color, style is about 1.75 mm in length and NN155C to NN155D in color, ovary is 147B in color.

*Androcoecium.*—About 4 stamens, anthers are oblong in shape, basifixed, paired, about 2.5 mm in length and 155A in color, filaments are about 1.3 cm in length and NN155C to NN155D in color, pollen is low in quantity and 161B to 161C in color.

*Fruit and seed.*—No fruit or seed have been observed.

It is claimed:

1. A new and distinct cultivar of *Abelia* plant named 'Wevo1' as herein illustrated and described.

* * * * *